United States Patent [19]

Shiroto et al.

[11] Patent Number: 4,950,824
[45] Date of Patent: Aug. 21, 1990

[54] PROCESS FOR THE PRODUCTION OF 2,6-DIISOPROPYLNAPHTHALENE

[75] Inventors: Yoshimi Shiroto; Mitsunori Shimura; Kenji Shimokawa, all of Yokohama; Yoshio Fukui, Tokyo; Sachio Asaoka, Yokohama; Hiroto Tajima, Kamakura; Kazuaki Ueda, Kawasaki; Yakudo Tachibana, Kasukabe; Kazuhiko Tate, Yokohama; Hiroaki Taniguchi, Kuki, all of Japan

[73] Assignees: Chiyoda Corporation; NKK Corporation, both of Japan

[21] Appl. No.: 388,393

[22] Filed: Aug. 2, 1989

[30] Foreign Application Priority Data

Sep. 26, 1988 [JP] Japan .................................. 63-242091
Dec. 26, 1988 [JP] Japan .................................. 63-328473

[51] Int. Cl.$^5$ .......................... C07C 4/00; C07C 2/64; C07C 2/66; C07C 7/12
[52] U.S. Cl. ..................................... 585/320; 585/323; 585/449; 585/450; 585/456; 585/466; 585/474; 585/467; 585/475; 585/828
[58] Field of Search ............... 585/320, 323, 449, 450, 585/459, 466, 467, 474, 475, 828

[56] References Cited

U.S. PATENT DOCUMENTS

| 2,592,587 | 4/1952 | Nickels | 585/450 |
| 2,985,589 | 5/1961 | Broughton et al. | 210/34 |

FOREIGN PATENT DOCUMENTS

| 50-10589 | 4/1975 | Japan | 585/474 |
| 50-33056 | 10/1975 | Japan | 585/474 |

Primary Examiner—H. M. Sneed
Assistant Examiner—James Saba
Attorney, Agent, or Firm—Lorusso & Loud

[57] ABSTRACT

A process for the production of 2,6-diisopropylnaphthalene is disclosed wherein an isopropylation reaction mixture containing isopropylated naphthalenes is subjected to transalkylation with a triisopropylnaphthalene-containing mixture to obtain a mixture containing mono-, di- and tri-isopropylnaphthalenes which is then separated into a first fraction containing monisopropylnaphthalenes, a second fraction containing diisopropylnaphthalenes and a third fraction containing triisopropylnaphthalenes. The first and third fractions are recycled to the above system, while the second fraction is subjected to separation treatments for the recovery of 2,6-diisopropylnaphthalene. The second fraction from which 2,6-diisopropylnaphthalene has been removed is subjected to transalkylation with naphthalene to obtain a monoisopropylnaphthalene-rich mixture which is to be fed to the isopropylation step.

31 Claims, 4 Drawing Sheets

PROCESS FOR THE PRODUCTION OF 2,6-DIISOPROPYLNAPHTHALENE

BACKGROUND OF THE INVENTION

It is well known that the reaction of naphthalene with propylene gives 2,6-diisopropylnaphthalene which is an important raw material for the production of 2,6-naphthalenedicarboxylic acid which in turn is useful for the fabrication of polyesters. Known processes are, however, not fully satisfactory from industrial point of view, since the reaction also yields a significant amount of other structural isomers, monoisopropylnaphthalenes and triisopropylnaphthalenes. It is also known to subject the reaction mixture obtained by the above isopropylation reaction to transalkylation conditions to convert monoisopropylnaphthalenes to diisopropylnaphthalenes. While such transalkylation can improve the yield of di-substituted products, the yield of the desired 2,6-substituted product is still unsatisfactory. Further, it is very difficult to isomerize diisopropylnaphthalenes to 2,6-diisopropylnaphthalene. Thus, there is a great demand for a process which can give 2,6-diisopropylnaphthalene with a high yield.

SUMMARY OF THE INVENTION

It is, therefore, the prime object of the present invention to provide a process which can give 2,6-diisopropylnaphthalene with a high yield.

It is a special object of the present invention to provide a process which can minimize the production of high boiling point substances such as triisopropylnaphthalenes.

In accomplishing the foregoing object, there is provided in accordance with the present invention a process for the production of 2,6-diisopropylnaphthalene, comprising the steps of:

(a) reacting a monoisopropylnaphthalene-containing feed with propylene to obtain a first mixture containing isopropylated naphthalenes;

(b) subjecting said first mixture to transalkylation with a triisopropylnaphthalene-containing mixture to obtain a second mixture containing mono-, di- and triisopropylnaphthalenes;

(c) separating said second mixture by distillation into a first fraction containing monoisopropylnaphthalenes, a second fraction having a higher boiling point than that of said first fraction and containing diisopropylnaphthalenes and a third fraction having a boiling point higher than that of said second portion and containing triisopropylnaphthalenes;

(d) recycling at least part of said third fraction to step (b) as said triisopropylnaphthalene-containing mixture;

(e) separating said second fraction into a first product rich in 2,6-diisopropylnaphthalene and a second product rich in diisopropylnaphthalenes other than 2,6-diisopropylnaphthalene;

(f) subjecting said second product to transalkylation with naphthalene to obtain a third mixture containing monoisopropylnaphthalenes; and (g) recycling said third mixture to step (a), as at least a portion of said monoisopropylnaphthalene-containing feed, and/or step (c) with the proviso that when said third mixture is recycled only to step (c), at least part of said first fraction obtained in step (c) is recycled to step (a) as said monoisopropylnaphthalene-containing feed.

In another aspect, the present invention provides a process for the production of diisopropyl-naphthalenes, comprising the steps of:

(a) reacting naphthalene with propylene to obtain a first mixture containing isopropylated naphthalenes, step (a) being carried out under conditions so that the molar ratio of the isopropyl groups of the isopropylated naphthalenes to the isopropylated naphthalenes and unsubstituted naphthalene contained in said first mixture is in the range of 1.3 : 1 to 1.8 : 1;

(b) subjecting said first mixture to transalkylation with a triisopropylnaphthalene-containing mixture to obtain a second mixture containing mono-, di- and triisopropylnaphthalenes;

(c) separating said second mixture by distillation into a first fraction containing monoisopropylnaphthalenes, a second fraction having a higher boiling point than that of said first fraction and containing diisopropyl-naphthalenes and a third fraction having a boiling point higher than that of said second portion and containing triisopropylnaphthalenes;

(d) recycling at least part of said third fraction to step (b) as said triisopropylnaphthalene-containing mixture; and (e) recycling at least part of said first fraction to step (a) or step (b).

BRIEF DESCRIPTION OF THE DRAWINGS

Other objects, features and advantages of the present invention will become apparent from the detailed description of the invention which follows, when considered in light of the accompanying drawings, in which.

DETAILED DESCRIPTION OF THE INVENTION

Figure 1:
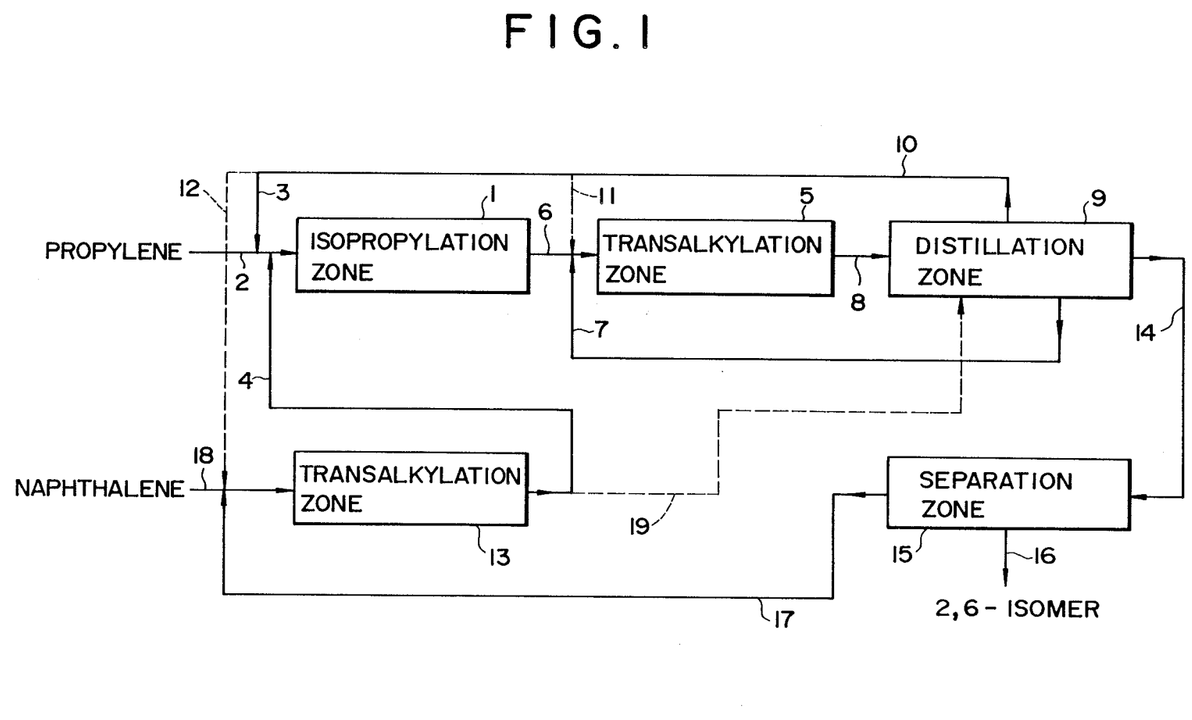
FIG. 1 is a flow diagram showing one embodiment according to the present invention.

Referring first to FIG. 1, designated as 1 is a reaction zone where propylene supplied through a line 2 is reacted with a hereinafter described monoisopropylnaphthalene-containing feed supplied through a line 3 and/or line 4 to obtain a first mixture containing isopropylated naphthalenes.

The isopropylation reaction may be performed in a liquid phase or a vapor phase using a Friedel-Craft catalyst such as aluminum chloride, hydrogen fluoride or phosphoric acid, or a solid acid catalyst such as silica-alumina, crystalline aluminosilicate, nickel oxide-silica, silver oxide-silica-alumina, silica-magnesia, alumina-boria, solid phosphoric acid, aluminum phosphate or zirconium phosphate.

When the Friedel-Craft catalyst is used, the isopropylation is generally performed at a temperature of 10°–150 ° C., preferably 50°–100° C., and a pressure of about 1–10 atm, with a weight ratio of the catalyst to the total reactants of 0.0001–0.3, preferably 0.02–0.2. In the case of the solid acid catalyst, the reaction is performed at a temperature of 150°–500 ° C., preferably 150°–350° C., and a pressure of 0–50 kg/cm$^2$G, preferably 0–35 kg/cm$^2$G for a contact time of 0.02–6 hours, preferably 0.4–2.5 hours. In either case, too high a temperature or too long a reaction time in excess of the above-specified ranges causes decomposition reactions to occur so that by-products are unadvantageously yielded in an increased amount. On the other hand, when the reaction temperature is lower or when the reaction time is shorter than the above-specified ranges, the yield of the diisopropylnaphthalenes becomes low.

For the purpose of obtaining 2,6-diisopropylnaphthalene with a high yield, it is especially preferred that the isopropylation reaction be performed in the presence of a solid acid catalyst, such as exemplified above, at a temperature of 150°–250 ° C. under a pressure so that naphthalene if any is present substantially as a liquid. In this case, when a zeolite catalyst (H-type) is used as the solid acid catalyst, it is also preferable to perform the isopropylation in the presence of water for reasons of minimizing or preventing the formation of coke on the solid catalyst. This can be accomplished, for example, by incorporating steam or water into the propylene feed through the line 2. The amount of the water in the reaction zone 1 is preferably 0.01–10%, more preferably 0.1–1% based on the weight of the liquid phase in the reaction zone 1. The reaction zone 1 may be a packed tower having a packed layer of the solid catalyst through which propylene gas and other raw material liquid feed are passed.

The first mixture obtained in the reaction zone 1 generally contains naphthalene, monoisopropylnaphthalenes, diisopropylnaphthalenes, triisopropylnaphthalenes and polyisopropylnaphthalenes with four or more isopropyl groups. The isopropyl groups on a naphthalene nucleus are easily reversibly transferred to another nucleus (intermolecular transalkylation) and a chemical equilibrium exists between the raw material and the product. The yield of the diisopropylnaphthalenes depends generally upon the molar ratio of naphthalene nuclei to isopropyl groups in the reaction system, temperature, and type catalyst.

It is preferred that the reaction conditions be controlled so that the first mixture has a molar ratio of naphthalene nuclei to isopropyl groups of 0.5 to 1.9, more preferably 0.7–1.8. This can be accomplished by, for example, controlling the reaction time or of the feed rate of propylene.

The first mixture discharged from the reaction zone 1 is then fed to a first transalkylation zone 5 through a line 4 where the first mixture is subjected to transalkylation with a hereinafter described, triisopropylnaphthalene-containing mixture supplied through a line 7 to obtain a second mixture containing mono-, di- and tri-isopropylnaphthalenes. That is, the non-substituted naphthalene and the mono-isopropylnaphthalenes contained in the first mixture are converted by intermolecular transalkylation with the tri-isopropylnaphthalenes into di-isopropylnaphthalenes. During the course of the transalkylation in the zone 5, isomerization of diisopropylnaphthalenes occurs at the same time. There is an equilibrium in proportions of respective isomers in the second mixture.

The transalkylation is performed using nearly the same conditions and catalysts. However, it is preferable to use more severe reaction conditions, e.g. higher temperature and a larger amount of the catalyst, as compared in those in the isopropylation step. The transalkylation can be carried out using a reactor separate from the reactor in which the isopropylation is performed. Alternately, the isopropylation and transalkylation can be conducted in a single reactor. The transalkylation is generally performed for 5–300 minutes, preferably 15–20 minutes. For the purpose of increasing the yield of 2,6-diisopropylnaphthalene, it is preferred that the transalkylation in the zone 5 be performed in the presence of a solid acid catalyst, such as exemplified above, at a temperature of 250°–300° C. under a pressure so that unreacted naphthalene if any is present substantially as a vapor.

Polyisopropylnaphthalenes having four or more isopropyl groups when present in a large amount in the transalkylation zone 5 causes the production of isopropyltetralin or other by-products. To minimize the formation of such by-products, the transalkylation is suitably carried out while maintaining the molar ratio of the isopropyl groups to naphthalene nuclei contained in the whole raw material feed (all the materials fed to the zone 5 inclusive of those of recycled streams) at 1.9 or less, more preferably at 1.0–1.8.

The second mixture discharged from the first transalkylation zone 5 is fed through a line 8 to a first separation zone 9 where the second mixture is separated by distillation into a first fraction containing monoisopropylnaphthalenes, a second fraction having a higher boiling point than that of the first fraction and containing diisopropyl-naphthalenes and a third fraction having a boiling point higher than that of the second fraction and containing triisopropylnaphthalenes.

The first fraction is discharged from the first separation zone 9 through a line 10 and is preferably supplied to at least one of (a) the first transalkylation zone 5 through a line 11, (b) the isopropylation zone 1 through the line 3 as described previously, and (c) a second transalkylation zone 13 described hereinafter through a line 12. In this case, it is preferred that the first fraction be separated into a light fraction and a heavy fraction and the light fraction alone be fed to (a), (b) and/or (c).

The third fraction is discharged from the first separation zone 9 through the line 7 and is recycled to the first transalkylation zone 5 as the previously described, triisopropylnaphthalene-containing mixture. In this case, too, it is preferred that the third fraction be separated into a light fraction and a heavy fraction and the light fraction alone be fed to the zone 5.

The second fraction containing diisopropylnaphthalenes such as 1,6-, 1,7-, 1,4-, 2,6-, 2,7-, 1,5-, 1,3- and 2,3-diisopropylnaphthalenes is discharged from the first separation zone 9 and is fed through a line 14 to a second separation zone 15 where the second fraction is separated into a first product relatively rich in 2,6-diisopropylnaphthalene and a second product relatively rich in diisopropylnaphthalenes other than 2,6-diisopropylnaphthalene. The separation may be effected by crystallization, chromatography or any other suitable method.

The first product is discharged from the zone 15 through a line 16 for recovery. The second product is discharged from the separation zone 15 and is introduced into the second transalkylation zone 13 through a line 17, where it is subjected to transalkylation with naphthalene fed through a line 18 and, optionally, through the line 12, thereby to obtain a third mixture containing monoisopropylnaphthalenes.

The naphthalene which may be one obtained from petroleum or coal is reacted with the diisopropylnaphthalenes to form monoisopropylnaphthalenes in the second transalkylation zone 13. The transalkylation in the zone 13 may be carried out in a manner similar to that in the first zone 5. It is preferred that the molar ratio of the isopropyl groups to the naphthalene nuclei in the whole raw material feed (raw materials supplied to the zone 13 through lines 18, 17 and, if it is the case, 12) be maintained in the range of 0.5–1.6, more preferably 0.8–1.4. For the purpose of increasing the yield of 2,6-diisopropylnaphthalene, the transalkylation in the zone 13 be performed in the presence of a solid acid catalyst, such as exemplified above, at a temperature of 250°–300° C. under a pressure so that the naphthalene is present substantially as a vapor.

The third mixture is discharged from the second transalkylation zone 13 and is introduced into the reaction zone 1 as at least a portion of the monoisopropyl-naphthalene-containing feed through the line 4 and/or the first separation zone 9 through a line 19. In this case, when the third mixture is recycled only to the first separation zone 9, at least part of the first fraction obtained in first separation zone 9 is recycled to the reaction zone 1 through the line 3 as the monoisopropyl-naphthalene-containing feed. A portion of the third mixture may be fed to the first transalkylation zone 5, if desired.

In the above first embodiment, the raw material naphthalene is fed to the second transalkylation zone 13. However, if desired, a portion of the naphthalene may be introduced into the reaction zone 1 and/or into the first transalkylation zone 5.

Figure 2:
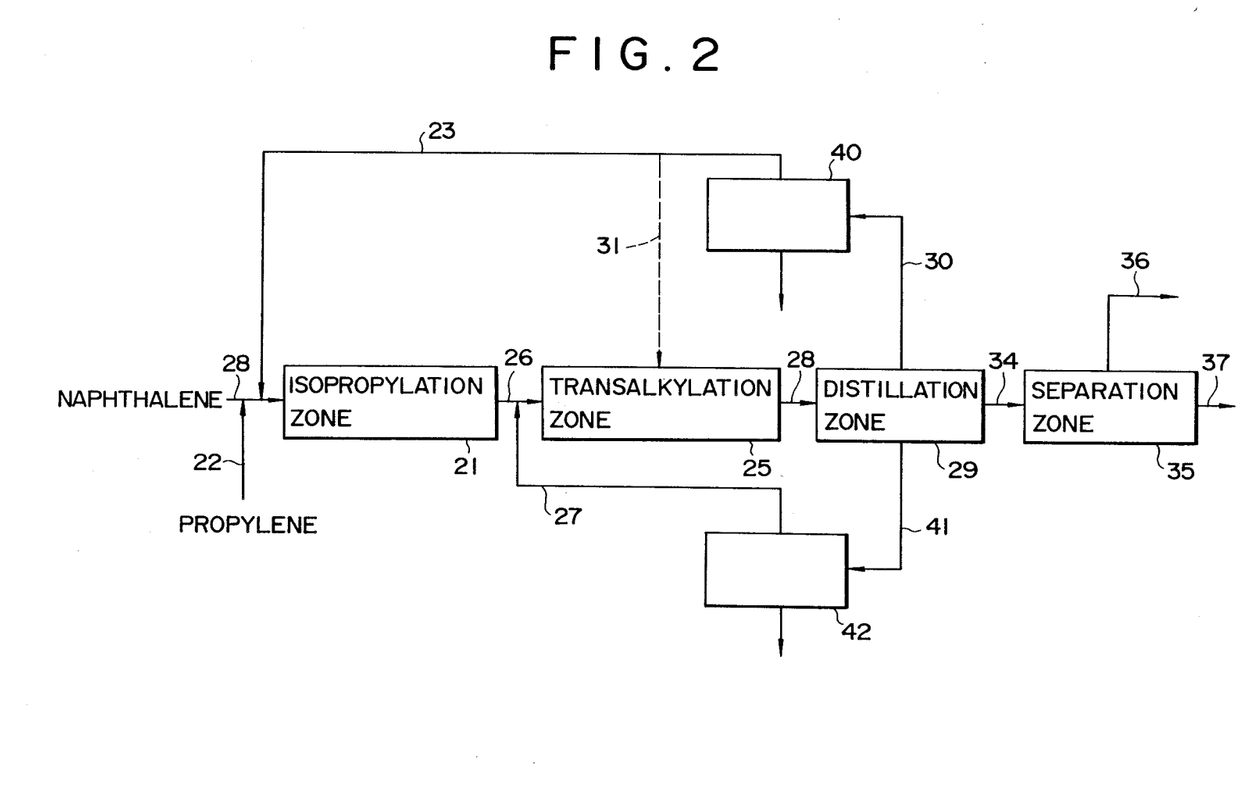
FIG. 2 is a flow diagram showing another embodiment according to the present invention.

Referring next to FIG. 2, designated as 21 is a reaction zone where naphthalene supplied through a line 28 is reacted with propylene supplied through a line 22 to obtain a first mixture containing isopropylated naphthalenes. The reaction in the reaction zone 21 is carried out under conditions so that the molar ratio of the isopropyl groups to the naphthalene nuclei contained in the first mixture is in the range of 1.3–1.8, preferably 1.4–1.6. A molar ratio of above 1.8 is disadvantageous because polyisopropylated naphthalenes containing 4 or more isopropyl groups are produced in a large amount so that by-products such as alkylnaphthalenes other than isopropylated naphthalenes and isopropyltetralin are produced in a large amount in the succeeding transalkylation stage. In accordance with the present invention the amount of such polyisopropylated naphthalenes in the first mixture can be reduced to 30 mole % or less. Too low a molar ratio below 1.3, on the other hand, causes the reduction of the yield of the desired diisopropyl-naphthalene. The control of the molar ratio may be accomplished by control of the reaction time and feed rates of propylene and naphthalene.

The isopropylation in the reaction zone 21 may be carried out in the same manner as that in the zone 1 of the previously described first embodiment. It is preferred that the isopropylation be performed in the presence of a solid acid catalyst at a temperature of 150°–250° C. under a pressure so that the naphthalene is present substantially as a liquid.

The first mixture obtained in the reaction zone 21 generally contains unreacted naphthalene, mono-, di- and tri-isopropylated naphthalenes and polyisopropyl-naphthalenes having four or more isopropyl groups. The first mixture is then fed to a transalkylation zone 25 through a line 26, where it is subjected to transalkylation with a triisopropylnaphthalene-containing mixture supplied through a line 27 to obtain a second mixture containing mono-, di- and tri-isopropylnaphthalenes. The transalkylation in the zone 25 can be performed in the same manner and conditions as those in the first transalkylation zone 5 of the above-described first embodiment. However, it is preferable to control the molar ratio of the isopropyl groups to the naphthalene nuclei in the whole raw material feed (not only the feed through the line 26, but also the feed through the line 27 and, if it is the case, a line 31) at 2.0 or less, more preferably 1.6–2.0, for reasons of suppressing the formation of the above-mentioned by-products. Preferably the transalkylation is performed in the presence of a solid acid catalyst at a temperature of 250°–300° C. under a pressure so that unreacted naphthalene if any is present substantially as a vapor.

The second mixture discharged from the transalkylation zone 25 is fed through a line 28 to a first separation zone 29 where the second mixture is separated by distillation into a first fraction containing monoisopropyl-naphthalenes, a second fraction having a higher boiling point than that of the first fraction and containing diisopropyl-naphthalenes and a third fraction having a boiling point higher than that of the second fraction and containing triisopropylnaphthalenes.

The first fraction is discharged from the first separation zone 29 through a line 30 and is preferably supplied to at least one of the transalkylation zone 25 through a line 31 and the isopropylation zone 21 through a line 23 In this case, it is preferred that the first fraction be separated in a fractionating zone 40 into a light fraction and a heavy fraction and the light fraction alone be fed to the transalkylation zone 25 and/or reaction zone 21.

The third fraction is discharged from the first separation zone 29 through a line 41 and is recycled to the transalkylation zone 25 as the previously described, triisopropylnaphthalene-containing mixture. In this case, too, it is preferred that the third fraction be separated in a suitable fractionating zone 42 into a light fraction and a heavy fraction and the light fraction alone be fed to the zone 25.

The second fraction containing diisopropylnaphthalenes such as 1,6-, 1,7-, 1,4-, 2,6-, 2,7-, 1,5-, 1,3- and 2,3-diisopropylnaphthalenes is discharged from the first separation zone 29 and is fed through a line 34 to a second separation zone 35 where the second fraction is separated into a first product relatively rich in 2,6-diisopropylnaphthalene and a second product relatively rich in diisopropylnaphthalenes other than 2,6-diisopropyl-naphthalene. The separation may be effected by crystallization, chromatography or any other suitable method. The first product is discharged through a line 36 and recovered while the second product may be recycled to the transalkylation zone 25, if desired.

The separation of the 2,6-diisopropylnaphthalene from the second fraction obtained in the separation zone 9 (FIG. 1) or 29 (FIG. 2) is suitably effected by a method including the steps of:

(a) subjecting said mixture to a selective adsorption and desorption treatment using a first zeolite absorbent capable of adsorbing the 2,7-isomer to obtain a first extract containing the sorbed 2,7-isomer and a first raffinate containing non-sorbed isomers including the 2,6-isomer; and (b) separating the 2,6-isomer from said first raffinate.

In one preferred embodiment, the first zeolite absorbent is capable of selectively adsorbing both 1,7- and 2,7-isomers so that the 1,7- and 2,7-isomers are removed from said mixture as the first extract, and the recovery of the 2,6-isomer from the first raffinate (step (b)) is effected by subjecting the first raffinate to a selective adsorption and desorption treatment using a second zeolite absorbent capable of adsorbing the 2,6-isomer to remove the 2,6-isomer therefrom as an extract and to obtain a second raffinate containing non-sorbed isomers. The first extract may be subjected to a distillation treatment to separate the 1,7- and 2,7-isomers from each other, as desired.

Each of the first and second zeolite absorbents is preferably an X-type or Y-type, Faujasite zeolite having a $SiO_2/Al_2O_3$ molar ratio of 2-6. The first zeolite absorbent is preferably a zeolite of the above-mentioned type having at least 80 mole %, more preferably at least 90 mole % of its exchangeable cations ion-exchanged with at least one cation selected from the group consisting of Li, Na, K, Ba and Pb ions. Especially preferred is an Y-type zeolite ion-exchanged with K and/or Li ions. The second zeolite absorbent is preferably a zeolite of the above-mentioned type having at least 80 mole % of its exchangeable cations ion-exchanged with at least one cation selected from the group consisting of Na, Pb and Ba. Especially preferred is an Y-type zeolite ion-exchanged with Na and/or Pb ions. The use of a zeolite absorbent containing proton is not recommended because it can act as a transalkylation catalyst of the di-isomers so that the yield of the 2,6-isomer is lowered.

The first and second zeolite absorbent preferably have a particle size of 3-300 mesh (Tyler). It is preferred that each of the first and second zeolite absorbents have a moisture content of 5% by weight or less, more preferably 3% by weight or less, when measured in terms of ignition loss at 1000° C., for reasons of improved adsorption selectivity and efficiency. Moisture contained in the zeolite absorbent is located in the cationic active site or within pores thereof, so that the weight of a substance adsorbed per unit weight of the absorbent is decreased.

The selective adsorption and desorption treatment in each of steps (a) and (b) is preferably performed at a temperature of about 50-300° C., more preferably about 80-200° C. and such a pressure that a mixture to be treated is present in a liquid state and may be effected by a method including the steps of:

(i) contacting a mixture to be treated with the zeolite absorbent contained in an adsorption zone and maintained at adsorption conditions to effect selective adsorption of a target isomer contained in the mixture;

(ii) withdrawing a raffinate containing non-sorbed isomers from the adsorption zone;

(iii) contacting the zeolite absorbent carrying the sorbed, target isomer and maintained at desorption conditions with a desorbent material to effect removal of the target isomer therefrom; and (iv) withdrawing from the zeolite absorbent an extract containing the removed target isomer.

As the desorbent material may be used a substance capable of being quickly adsorbed by the absorbent material for replacement for the sorbed target isomer. An aromatic desorbent material, especially an alkylbenzene of the formula:

(R')$_n$—Ph—R wherein Ph represents a benzene nucleus, R and R' represent independently from each other a methyl, an ethyl, an n-propyl or an isopropyl, and n is an integer of 0 or 1, is suitably used.

The above adsorption and desorption treatment is advantageously carried out using a simulated, countercurrent moving bed system. By this, there is obtainable 2,6-isomer having a purity of as high as 99% or more. Such a moving bed system per se is known in the art and is applied for selective removal of a specific xylylene compound from its isomers (Japanese Examined Publication (Tokyo Kokoku) No. 42-15681 and No. 50-10547).

Figure 3:
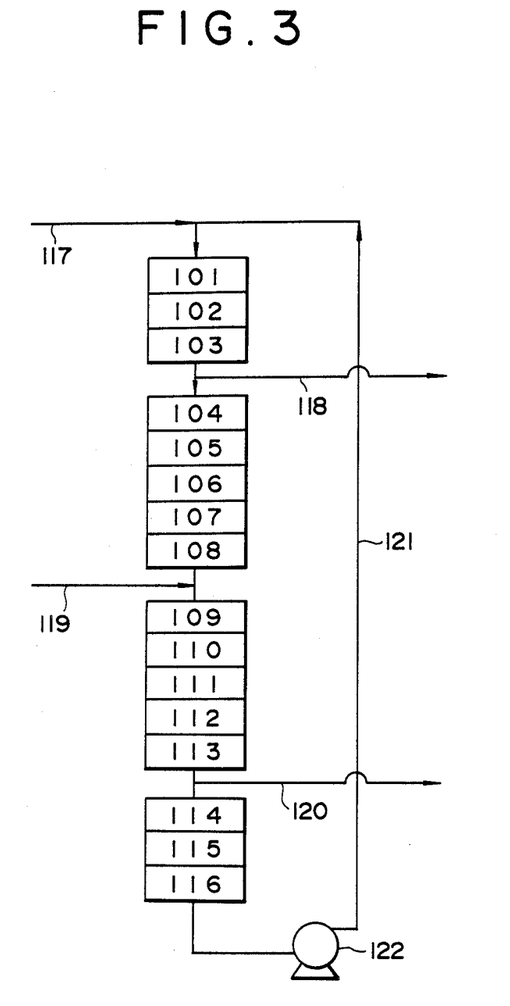
FIG. 3 is a diagram showing a simulated, countercurrent moving bed system useful for carrying out the separation of diisopropylnaphthalene isomers.

One example of such a simulated countercurrent moving bed system is shown in FIG. 3. The system includes a fixed bed of a said first zeolite absorbent containing at least four serially interconnected zones (16 zones in the specifically illustrated case) having fluid flow connecting means between adjacent zones and between the outlet of the last zone and the inlet of the first zone in the series, to thereby provide cyclic, fluid flow. Designated at 122 is a pump for causing the fluid flow in the direction shown by the arrow.

In the system, four different operations, i.e. adsorption of a target isomer, concentration of the adsorbed target isomer, desorption of the adsorbed target isomer using a desorbing material, and recovery of the desorbing material are being simultaneously carried out in the respective zones.

In the illustrated stage, the zones 101-103 are performing the desorption, the zones 104-108 are performing the concentration, the zones 109-113 are performing the adsorption and the zones 114-116 are performing the recovery. That is, a mixture to be treated is introduced through a line 119 into one, sorbing zone 109 and then into succeeding zones 110-113 to selectively sorb the target isomer contained in the mixture.

The desorbent material is fed through a line 117 to a desorbing zone 101 and is passed through the zones 102 and 103 to remove the adsorbed target isomer. The desorbing zones 101-103 are positioned upstream of the adsorbing zones 109-113 such that intermediate, concentrating zones 104-108 are defined between the adsorbing zones 109-113 and desorbing zones 101-103 and that recovering zones 114-116 are defined downstream of the adsorbing zones 109-112.

At the same time, the mixture from which the target isomer has been removed by adsorption and which contains non-sorbed isomers is withdrawn from the fluid flow connecting means extending between the adsorbing zone 113 and the recovering zone 114 through a line 120 as a raffinate. Further, the removed target isomer is simultaneously withdrawn from the fluid flow connecting means extending between the desorbing zone 103 and the concentrating zone 104 through a line 118 as an extract.

A portion of the removed target isomer is fed from the desorbing zone 103 to the concentrating zones 104-108 and is replaced for the sorbed isomers other than the target isomer on the absorbent. The absorbent which has sorbed the desorbent material is contacted in the recovery zones 114-116 with a portion of non-sorbed isomers for replacement therewith. The thus recovered desorbent material is fed to the desorbing zones 101-103.

The point of introducing the mixture to be treated is periodically advanced downstream, while simultaneously and equally advancing the points of introducing the desorbent material and of withdrawing the raffinate and the extract. Therefore, in the next stage succeeding the illustrated stage, the desorption, concentration, adsorption and recovery are effected in the zones 102-104, 105-109, 110-114 and 115-101. Thus, though the bed of the absorbent is fixed in the treatment tower, there is established a system similar to a countercurrent moving bed by periodically advancing the introduction and withdrawing points downstream with respect to the fluid flow.

In the above-described first embodiment involving the two stage adsorption and desorption treatment, the first raffinate obtained in the first stage can be fed to the second stage as such or after removing the desorbent material contained therein. When 2,6-isomer is separated from the isomeric mixture by a one-stage adsorption and desorption treatment, it is necessary to select a specific absorbent and to use an absorbing tower having a large number of absorption steps and a large amount of absorbent. In contrast, the use of the two stage treatment in accordance with the present invention, the absorbent can be selected without difficulty and the process can be performed at a high speed without using an adsorption column with a relatively small number of steps.

Figure 4:
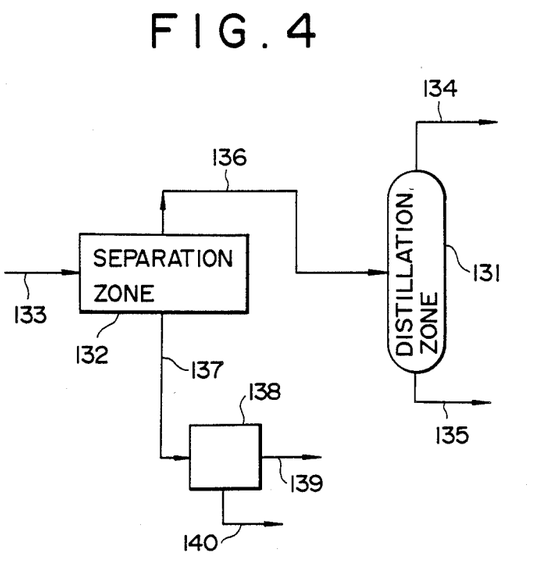
FIGS. 4 and 5 are flow diagrams for effecting separation of specific diisopropylnaphthalene isomers by a combination of distillation and adsorption.

FIG. 4 shows a second embodiment according to the present invention, in which the isomeric mixture from a line 133 is subjected to an adsorption and desorption treatment in a zone 132 containing an absorbent capable of adsorbing 2,7- and 1,7-isomers, thereby to obtain an extract containing the 2,7- and 1,7-isomers through a line 136 and a raffinate through a line 137. The extract is then introduced into a distillation zone 131 to separate the extract into the 1,7-isomer as a distillation top through a line 134 and the 2,7-isomer as a bottom product through a line 135. The raffinate is fed to a separation zone 138 to isolate the 2,6-isomer through a line 139. The other isomers are recovered through a line 140.

Figure 5:
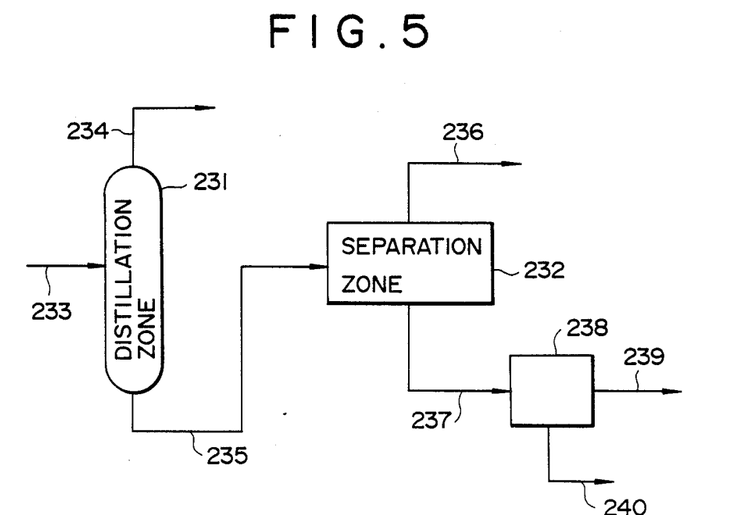

FIG. 5 shows a third embodiment according to the present invention, in which the isomeric mixture from a line 233 is first introduced into a distillation zone 231 to separate the 1,3- and 1,7-isomers therefrom through a line 234. The resulting mixture from which the 1,3- and 1,7-isomers have been removed is fed through a line 235 to a selective adsorption and desorption treatment zone 232, preferably of a simulated, countercurrent moving bed system as described above, containing an absorbent capable of adsorbing the 2,7-isomer, thereby to obtain a first extract containing the sorbed 2,7-isomer (line 236) and a first raffinate containing non-sorbed isomers including the 2,6-isomer. The 2,6-isomer is then fed through a line 237 to a separation zone 238 to isolate the 2,6-isomer through a line 239. The other isomers are recovered through a line 240.

As separation method in the separation zone 138 or 238, there may be adopted a precipitation method (disclosed, for example, in Japanese Published Unexamined patent application (Tokyo Kokai) No. 62-226931), an inclusion method (disclosed, for example, in Tokyo Kokai No. 63-88141) or an adsorption and desorption method such as described above.

The adsorption and desorption treatment in the zone 132 or 232 is preferably carried out by using a simulated, countercurrent moving bed system as described above. For the reasons as set forth below, the desorbing, concentrating, sorbing and recovering zones are preferably operated under conditions satisfying the following formulas:

desorbing zone: $L(I)/S(I) > 0.2 + L(IV)/S(I)$
concentrating zone: $L(II)/S(II) > 0.1 + L(IV)/S(II)$
sorbing zone: $L(III)/S(III) < 0.3 + L(IV)/S(III)$
recovering zone: $0.8 < L(IV)/S(IV) < 1.0$ wherein L(I) through L(IV) represent the flow rates, in terms of cc/hour, of liquids flowing through the desorbing zone, concentrating zone, sorbing zone and recovering zone, respectively, and S(I) through S(IV) represent the simulate moving rates, in terms of cc/hour, of the solid absorbent through the desorbing zone, concentrating zone, sorbing zone and recovering zone, respectively.

In the desorbing zone, the absorbent which has sorbed a high concentration of the 2,7-isomer (or both 2,7- and 1,7-isomers) is contacted with the desorbent material. If the liquid flow rate in this zone is too low to sufficiently desorb the 2,7 isomer, the 2,7-isomer contaminates the raffinate, resulting in the recovery rate of the 2,7-isomer. More preferably, the desorbing zone is operated under the following condition:

$$L(I)/S(I) > 0.25 + L(IV)/S(I)$$

In the concentrating zone, the isomers other than the 2,7-isomer (or 1,7 and 2,7-isomers) which have been sorbed by the absorbent are perfectly desorbed. If the liquid flow rate in this zone is too low to sufficiently desorb the isomers other than the 2,7-isomer, they contaminate the extract, lowering the purity of the 2,7-isomer extract product. A more preferred set of conditions is as follows:

$$L(II)/S(II) > 0.15 + L(IV)/S(II)$$

In the adsorption zone, the 2,7-isomer (or 1,7- and 2,7-isomers) contained in the isomeric mixture is sorbed by the absorbent while the other isomers are recovered as a raffinate together with the desorbent material. If the liquid flow rate is so high that the 2,7-isomer is not sufficiently sorbed by the absorbent, the 2,7-isomer is discharged from the absorption zone and is incorporated into the raffinate, resulting in the lowering of the 2,7-isomer recovery rate. A more preferred set of conditions is as follows:

$$L(III)/S(III) < 0.25 + L(IV)/S(III)$$

In the recovery zone, di-isomers from which the 2,7-isomer have been removed in the adsorption zone are adsorbed by the absorbent. The absorbent carrying the di-isomers is fed to the adsorption zone where the di-isomers are replaced by the more adsorptive 2,7-isomer and are recovered as the raffinate, as described above. The liquid flow discharged from the bottom of the recovery zone consists essentially of the desorbent material and no longer contains any di-isomers. The thus recovered desorbent material is then fed to the desorption zone. If the liquid flow rate is too high to sufficiently adsorb less adsorptive di-isomers, the di-isomers contaminate the desorbent material and, therefore, the extract, resulting in the lowering of the purity of the 2,7-isomer extract product. If, on the other hand, the liquid flow rate is excessively low, there is a danger that the di-isomers other than the 2,7-isomer are carried by the adsorbent and are passed successively to the adsorption zone, concentration zone and the desorption zone, thereby to contaminate the extract. A more preferred set of conditions is as follows:

$$0.8 < L(IV)/S(IV) < 0.95$$

The adsorptivity of diisopropylnaphthalenes on a zeolite absorbent relative to the 2,7-isomer may be expressed by a relative separation factor $\beta(2,7/i)$ defined by the following formula:

$$\beta(2,7/i) = K(2,7)/K(i)$$

wherein K(2,7) and K(i) represent solid/liquid equilibrium constants of the 2,7-isomer and an isomer "i", respectively, defined as follows:

$$K(2,7) = \frac{\text{Concentration (g/cc) of 2,7-isomer in adsorption phase}}{\text{Concentration (g/cc) of 2,7-isomer in liquid phase}}$$

$$K(i) = \frac{\text{Concentration (g/cc) of isomer "i" in adsorption phase}}{\text{Concentration (g/cc) of isomer "i" in liquid phase}}$$

An isomer whose $\beta(2,7/i)$ is smaller than 1 is more absorptive than the 2,7-isomer. Conversely, an isomer whose factor $\beta(2,7/i)$ is greater than 1 is more difficult to be adsorbed in comparison with the 2,7-isomer. The factor $\beta(2,7/1,7)$ of the 1,7-isomer for a zeolite absorbent is about 1, while those of the other isomers are greater than 1. Therefore, the 2,7- and 1,7-isomers can be separated from the other isomers by selective adsorption with the zeolite absorbent. It is preferable to use a zeolite absorbent providing the factor $\beta(2,7/i)$ of more than 2 for the isomers other than the 1,7- and 2,7 isomers. Further, it is preferable to use a desorbent material whose relative separation factor $\beta(2,7/D)$ is in the range of 0.5–3, more preferably 1–2 from the standpoint of economy. If the factor $\beta(2,7/D)$ becomes large in excess of 3, it is necessary to use a large amount of the desorbent material. On the other hand, a desorbent material whose factor $\beta(2,7/D)$ is smaller than 0.5 requires a large amount of the absorbent.

The following examples will further illustrate the present invention.

EXAMPLE 1

A mixture having the composition shown in Table 1 below was subjected to a transalkylation treatment at 85° C. under ambient pressure for 1 hour in the presence of 0.11 mol of an aluminum chloride catalyst per mole of naphthalene nucleus contained in the mixture.

TABLE 1

| Reactant | Content (% by weight) |
| --- | --- |
| Naphthalene | 33.9 |
| 2,7-diisopropylnaphthalene | 46.1 |
| 2,6-diisopropylnaphthalene | 0 |
| Other diisopropylnaphthalenes | 20.0 |

The above transalkylation gave a mixture having the composition shown in Table 2 below.

TABLE 2

| Reactant | Content (% by weight) |
| --- | --- |
| Naphthalene | 21.1 |
| Monoisopropylnaphthalene | 36.7 |
| 2,7-diisopropylnaphthalene | 15.7 |
| 2,6-diisopropylnaphthalene | 13.3 |
| Other diisopropylnaphthalenes | 5.9 |
| Triisopropylnaphthalenes | 7.3 |

The mixture of the composition shown in Table 2 was mixed with a hereinafter-described monoisopropylnaphthalene-rich fraction to give a mixture having the composition shown in Table 3. The resulting mixture was reacted with 0.35 mol of propylene per mole of naphthalene nucleus contained in the mixture at 85 °C. under ambient pressure in the presence of 0.11 mole of an aluminum chloride catalyst per mole of naphthalene nucleus contained in the mixture.

TABLE 3

| Reactant | Content (% by weight) |
| --- | --- |
| Naphthalene | 16.7 |
| Monoisopropylnaphthalene | 64.2 |
| 2,7-diisopropylnaphthalene | 4.6 |
| 2,6-diisopropylnaphthalene | 4.7 |
| Other diisopropylnaphthalenes | 6.5 |
| Triisopropylnaphthalenes | 3.3 |

The above isopropylation gave a reaction mixture having the composition shown in Table 4 below.

TABLE 4

| Reactant | Content (% by weight) |
| --- | --- |
| Naphthalene | 11.1 |
| Monoisopropylnaphthalene | 42.9 |
| 2,7-diisopropylnaphthalene | 9.3 |
| 2,6-diisopropylnaphthalene | 9.5 |
| Other diisopropylnaphthalenes | 13.3 |
| Triisopropylnaphthalenes | 13.9 |

The above reaction mixture was mixed with a hereinafter-described triisopropylnaphthalene-rich fraction to obtain a mixture having the composition shown in Table 5 below.

TABLE 5

| Reactant | Content (% by weight) |
| --- | --- |
| Naphthalene | 10.4 |
| Monoisopropylnaphthalene | 39.8 |
| 2,7-diisopropylnaphthalene | 8.7 |
| 2,6-diisopropylnaphthalene | 8.9 |
| Other diisopropylnaphthalenes | 12.6 |
| Triisopropylnaphthalenes | 19.6 |

The thus obtained mixture of Table 5 was subjected to a transalkylation treatment at 85° C. under ambient pressure for 1 hour in the presence of 0.11 mol of an aluminum chloride catalyst per mole of naphthalene nucleus contained in the mixture. As a result of the transalkylation, a mixture having the composition shown in Table 6 was obtained.

TABLE 6

| Reactant | Content (% by weight) |
| --- | --- |
| Naphthalene | 6.3 |
| Monoisopropylnaphthalene | 42.1 |
| 2,7-diisopropylnaphthalene | 18.3 |
| 2,6-diisopropylnaphthalene | 18.5 |
| Other diisopropylnaphthalenes | 7.2 |
| Triisopropylnaphthalenes | 7.6 |

The product having the composition of Table 6 was separated by distillation into the previously-described monoisopropylnaphthalene-rich fraction, a diisopropylnaphthalene-rich fraction and a the previously-described triisopropylnaphthalene-rich fraction. The diisopropylnaphthalene-containing fraction was subjected to a separation treatment for the recovery of 2,6-diisopropylnaphthalene. The other fractions were recycled as described previously.

EXAMPLE 2

To a reaction zone containing naphthalene and 0.11 mole of an aluminum chloride catalyst per mole of the naphthalene, propylene was fed at 85° C. under ambient pressure at a feed rate of 0.017 mole per minute per mole of the naphthalene for such a period of time as to provide an alkylation degree (IP/NP) shown in Table 7 below. In Table 7 and in the succeeding tables, the abbreviations are as follows:

NP : Naphthalene
MIPN : Monoisopropylnaphthalenes
DIPN : Diisopropylnaphthalene
PIPN : Polyisopropylnaphthalenes (Tri- or higher)
TEIPN : Tetraisopropylnaphthalene
IPEN : Alkylnaphthalenes other than isopropylated ones
IPTL : Isopropyltetralin
IP/NP : Molar ratio of isopropyl group to naphthalene nucleus in the isopropylation product (or transalkylation product)

TABLE 7

| Experiment No. | Content (molar %) | | | | |
|---|---|---|---|---|---|
| | 1 | 2 | 3 | 4 | 5 |
| Isopropylation product | | | | | |
| NP | 38.4 | 32.1 | 27.0 | 20.1 | 16.0 |
| MIPN | 31.9 | 30.7 | 28.9 | 25.2 | 22.5 |
| DIPN | 18.8 | 21.5 | 23.6 | 24.3 | 24.2 |
| PIPN | 10.8 | 15.7 | 20.5 | 30.4 | 37.3 |
| IPEN | — | — | — | — | — |
| IPTL | — | — | — | — | — |
| IP/NP (Molar ratio) | 1.0 | 1.3 | 1.5 | 1.8 | 2.0 |
| Transalkylation product | | | | | |
| NP | 14.2 | 8.4 | 6.8 | 2.4 | 1.5 |
| MIPN | 41.6 | 33.8 | 30.9 | 22.7 | 17.6 |
| DIPN | 36.9 | 42.4 | 45.2 | 49.8 | 45.2 |
| PIPN | 4.0 | 11.6 | 13.0 | 20.3 | 30.3 |
| IPEN | 2.2 | 2.5 | 2.7 | 3.2 | 3.5 |
| IPTL | 1.1 | 1.6 | 1.7 | 2.0 | 2.2 |
| IP/NP (Molar ratio) | 1.0 | 1.3 | 1.5 | 1.8 | 2.0 |

From the results shown above, it is apparent that the transalkylation of the isopropylation product with triisopropylnaphthalenes can improve the yield of diisopropylnaphthalenes, especially when the degree of alkylation (IP/NP) in the isopropylation stage is in the range of 1.3–1.8. The above results also suggest that the yield of by-products (IPEN and IPTL) and diisopropylnaphthalenes can be controlled by control of the feed rate of the triisopropylnaphthalenes.

EXAMPLE 3

Naphthalene and propylene, with a molar ratio of the former to the latter being 1:2, were fed to a reaction tower packed with a proton type Y-zeolite (H-Y-zeolite) and were passed downward therethrough at a temperature shown in Table 8, while simultaneously supplying steam in an amount of 1% by weight based on the naphthalene feed. The liquid space velocity of the naphthalene feed was set at 1.0 hr$^{-1}$. The propylene conversion, the yield of 2,6-diisopropylnaphthalene (2,6-DIPN) and the total yield of by-products (components having a boiling point of lower than 400° C. and other than naphthalene and diisopropylnaphthalene) and high boiling point products (components having a boiling point of 400° C. or more) are shown in Table 8 below.

TABLE 8

| Reaction temperature (°C.) | 150 | 180 | 210 | 240* | 270* |
|---|---|---|---|---|---|
| Propylene conversion (%) | 60 | 100 | 100 | 100 | 100 |
| Yield of 2,6-DIPN | 9.5 | 15.1 | 18.5 | 22.3 | 23.1 |
| Total yield of by-product and high boiling point product (% by weight) | 0.1 | 0.3 | 0.8 | 4.0 | 5.1 |

*Comparative example (naphthalene forms vapor phase)

The above isopropylation product obtained at a reaction temperature of 180° C. was fed to a reaction tower packed with an H—Y-zeolite catalyst similar to the above and was passed downward therethrough at a temperature shown in Table 9 with a liquid hourly space velocity of 0.5 hr$^{-1}$.

TABLE 9

| Reaction temperature (°C.) | 210 | 260 | 285 | 310* |
|---|---|---|---|---|
| Yield of 2,6-DIPN | 16.1 | 22.3 | 23.1 | 22.9 |
| Total yield of by-product and high boiling point product (% by weight) | 1.1 | 4.5 | 5.1 | 6.8 |

*Comparative example

EXAMPLE 4

Isopropylation and succeeding transalkylation were performed in the same manner as in Example 3 except that silica-alumina was used as a catalyst and that no steam was supplied in the isopropylation stage. The results are summarized in Table 10.

TABLE 10

| Reaction temperature (°C.) | 180 | 280 |
|---|---|---|
| Propylene conversion (%) | 100 | 100 |
| Yield of 2,6-DIPN | 7.6 | 18.3 |
| Total yield of by-product and high boiling point product (% by weight) | 0.0 | 1.6 |

TABLE 11

| Isopropylation temperature | 180 | 180 | 280 | 280 |
|---|---|---|---|---|
| Reaction temperature (°C.) | 220 | 280 | 220 | 280 |
| Yield of 2,6-DIPN | 12.8 | 21.5 | 18.5 | 21.4 |
| Total yield of by-product and high boiling point product (% by weight) | 0.2 | 2.1 | 1.6 | 3.5 |

EXAMPLE 5

Naphthalene (100 parts by weight) was mixed with 100 parts of diisopropylnaphthalenes (major component: 2,7-diisopropylnaphthalene) and the mixture was subjected to a transalkylation treatment using a packed reaction tower similar to that of Example 3 at a temperature of 240° C. and a pressure of 5 Kg/cm$^2$G. Nitrogen gas was used for increasing the pressure. The composition of the reaction product was as shown in Table 12.

TABLE 12

| Product | Content (% by weight) |
|---|---|
| NP | 22.4 |
| MIPN | 45.2 |
| DIPN | 31.0 |
| TIPN | 1.4 |
| TEIPN | 0.0 |
| High boiling point product | 0.0 |

EXAMPLE 6

1. Isopropylation:

An equimolar mixture of naphthalene and monoisopropylnaphthalenes and propylene were passed downward through a reaction tower packed with a silica-alumina catalyst at a feed rate of the mixture of 10 cc/hr and a feed rate of the propylene of 3 liter/hour to effect isopropylation at a temperature of 180 ° C. and a pressure of 2 Kg/cm$^2$G. The reaction product discharged from the bottom of the tower was analysed to give the results shown in Table 13.

TABLE 13

| Product | Content (% by (weight) |
|---|---|
| NP | 11.3 |
| MIPN | 18.3 |
| DIPN | 27.7 |
| TIPN | 30.1 |
| TEIPN | 9.5 |
| Others | 3.1 |
| Composition of DIPN | |
| 1,3-DIPN | 20.4 |
| 1,7-DIPN | 12.8 |
| 1,5-DIPN | 1.3 |
| 1,4-DIPN | 6.8 |
| 2,7-DIPN | 19.2 |
| 1,6-DIPN | 12.3 |
| 2,3-DIPN | 3.8 |
| 2,6-DIPN | 23.4 |

2. Transalkylation:

The above isopropylation product was mixed with TIPN to obtain a mixture having a TIPN content of 44% by weight. The mixture was then fed to a reaction tower packed with an H—Y—zeolite catalyst and passed downward therethrough to effect transalkylation at a temperature of 220° C. with a liquid hourly space velocity of 0.5 hr$^{-1}$. The product had a composition as shown in Table 14.

TABLE 14

| Product | Content (% by weight) |
|---|---|
| NP | 1.1 |
| MIPN | 15.3 |
| DIPN | 56.5 |
| TIPN | 23.1 |
| TEIPN | 0.5 |
| Others | 3.5 |
| Composition of DIPN | |
| 1,3-DIPN | 5.8 |
| 1,7-DIPN | 5.1 |
| 1,5-DIPN | 0.1 |
| 1,4-DIPN | 0.2 |
| 2,7-DIPN | 41.8 |
| 1,6-DIPN | 6.0 |
| 2,3-DIPN | 0.4 |
| 2,6-DIPN | 40.6 |

3. Distillation for Isolation of DIPN:

The product obtained by the above transalkylation was subjected to a distillation treatment to obtain a diisopropylnaphthalene fraction (99.4% by weight), a lower fraction having a boiling point lower than diisopropylnaphthalenes and a higher fraction having a boiling point higher than diisopropylnaphthalenes. Each of the lower and higher fractions was further separated by distillation into a light fraction and a heavy fraction. The composition of each of the DIPN fraction the light fractions of the lower and higher fractions was as shown in Table 15.

TABLE 15

| Component | Content (% by weight) |
|---|---|
| Composition of DIPN | |
| 1,3-DIPN | 5.7 |
| 1,7-DIPN | 5.0 |
| 1,5-DIPN | 0.1 |
| 1,4-DIPN | 0.2 |
| 2,7-DIPN | 41.5 |
| 1,6-DIPN | 5.8 |
| 2,3-DIPN | 0.3 |
| 2,6-DIPN | 40.7 |
| others | 0.6 |

TABLE 15-continued

| Component | Content (% by weight) |
|---|---|
| Composition of the light fraction of the lower fraction | |
| NP | 6.7 |
| MIPN | 92.5 |
| others | 0.8 |
| Composition of the light fraction of the higher fraction | |
| TIPN | 96.6 |
| TEIPN | 2.1 |
| Others | 1.3 |

4. Separation of 2,6- and 2,7-DIPN:

Separation of 2,6- and 2,7-DIPN from an isomeric mixture was performed in the following manner:

(a) Separation of 1,3- and 1,7-DIPN by Distillation:

A DIPN mixture (about 1.5 liters) having the composition shown in Table 16 was distilled using a batch type distillation tower (inside diameter: 20 mm, height: 1800 mm) packed with a McMahon packing under a pressure of 50 mmHg with a reflux ratio of 20. As a result, a distillation residue free of 1,3- or 1,7-DIPN having the composition shown in Table 17 was obtained.

TABLE 16

| Composition of DIPN | Content (% by weight) | Boiling Point (°C.) |
|---|---|---|
| 1,3-DIPN | 18.6 | 309 |
| 1,7-DIPN | 16.3 | 309 |
| 1,5-DIPN | 3.4 | 311 |
| 1,4-DIPN | 7.6 | 315 |
| 2,7-DIPN | 17.2 | 317 |
| 1,6-DIPN | 14.3 | 318 |
| 2,3-DIPN | 4.5 | 318 |
| 2,6-DIPN | 17.0 | 319 |
| others | 1.1 | — |

TABLE 17

| (distillation residue) | |
|---|---|
| Component | Content (% by weight) |
| 1,5-DIPN | 1.2 |
| 1,4-DIPN | 6.7 |
| 2,7-DIPN | 27.5 |
| 1,6-DIPN | 25.4 |
| 2,3-DIPN | 7.9 |
| 2,6-DIPN | 30.2 |
| others | 1.1 |

(b) Separation of 2,7-DIPN by Adsorption:

About 10 g of a sodium-type Y-zeolite (SiO$_2$/Al$_2$O$_3$ molar ratio: 4.6, particle size: 40–80 mesh) were mixed with about 100 g of a 0.5 mol/liter aqueous solution of a metal chloride and the mixture was allowed to stand at 90°–100° C. for 2 hours for effecting ion-exchange with the metal. After filtration, the precipitate was mixed again with the above aqueous solution and the mixture was heat-treated in the same manner. The above procedures were repeated once more and the precipitate was dried and calcined at 400° C. for 3 hours to obtain an absorbent ion-exchanged with K (Absorbent No. 1) or Na (Absorbent No. 2).

Into a 30 cc autoclave, about 4 g of the absorbent, about 6.5 g of the above distillation residue having the composition shown in Table 17 and about 1.5 g of diethylbenzene (desorbent material) were added and the mixture was stirred for 120 minutes at a constant temperature. The resulting mixture was filtered. The absorbent was washed with isooctane and then subjected to extraction with toluene by means of a Soxhlet extractor. The filtrate and the extracted material were each analyzed by gas chromatograph, from the results of which relative separation factors (2,7/i) were calculated. The results are shown in Table 18.

TABLE 18

| Absorbent | Ion Exchanged Metal | Relative Separation Factor β | | | | |
|---|---|---|---|---|---|---|
| | | (2,7/1,5) | (2,7/1,4) | (2,7/1,6) | (2,7/2,3) | (2,7/2,6) |
| No. 1 | K | 2.0 | 3.6 | 5.6 | 2.8 | 11.1 |
| No. 2 | Na | 2.0 | 9.6 | 3.3 | 2.0 | 1.3 |

(c) Separation of 2,6-DIPN:

About 100 g of an isomeric mixture which has been obtained by the above distillation (a) and extraction (b) treatment and having the composition shown in Table 19 were mixed with about 30 g of n-hexane and the mixture was cooled to 0° C. to precipitate crystals. Filtration gave about 30 g of 2,6-DIPN having a purity of 98.1%.

TABLE 19

| Component | Content (% by weight) |
|---|---|
| 1,5-DIPN | 1.6 |
| 1,4-DIPN | 9.2 |
| 1,6-DIPN | 35.0 |
| 2,3-DIPN | 11.0 |
| 2,6-DIPN | 41.7 |
| others | 1.5 |

EXAMPLE 7

Using absorbent No. 1 shown in Example 6, a mixture of 20 parts by weight of the DIPN mixture having the composition shown in Table 17 and 80 parts by weight of a desorbent material shown in Table 20 was subjected to an extraction treatment (b) as described in Example 6, thereby to obtain relative separation factors shown in Table 20.

TABLE 20

| Desorbent material | Relative Separation Factor β | | | | | |
|---|---|---|---|---|---|---|
| | (2,7/1,5) | (2,7/1,4) | (2,7/1,6) | (2,7/2,3) | (2,7/2,6) | (2,7/D) |
| PDPB*1 | 4.2 | 8.5 | 18.5 | 2.5 | 28.5 | 12.8 |
| DB*2 | 2.0 | 3.6 | 5.6 | 2.8 | 11.1 | 1.4 |
| p-Cymene | 6.3 | 7.5 | 6.3 | 2.0 | 12.5 | 1.3 |
| Ethylbenzene | 5.6 | 20.1 | 4.3 | 1.9 | 12.2 | 6.3 |
| Toluene | 7.0 | 20.0 | 3.0 | 1.1 | 10.0 | 15.0 |

*1: p-Diisopropylbenzene
*2: Diethylbenzene

EXAMPLE 8

The isomeric mixture having the composition shown in Table 17 was subjected to an adsorption and desorption separation treatment for the removal of 2,7-DIPN using a simulated, countercurrent moving bed system as shown in FIG. 3. Absorbent No. 1 (K-type Y-zeolite) was packed in 16 column chambers No. 101–116 (each inside volume: 70 ml). In the first stage, the isomeric mixture was fed through the line 119, a desorbent material (diethylbenzene) through the line 117, while simultaneously discharging an extract through the line 118 and a raffinate through the line 120. The points of the feeding and discharging were shifted downward from one chamber to the adjacent downstream chamber with a predetermined interval so that the stimulated displacing speed (S) of the absorbent was 818 cc/hour. The above procedure was carried out in various conditions (various feed rates and discharge rates) as shown in Table 21. The purity and recovery rate (yield) of 2,7-DIPN are shown in Table 21.

TABLE 21

| Experiment No. | 1 | 2 | 3 | 4 | 5 | 6 |
|---|---|---|---|---|---|---|
| Desorbent material feed rate (cc/hr) | 247 | 130 | 232 | 312 | 293 | 409 |
| Extract discharge rate (cc/hr) | 131 | 24 | 246 | 188 | 155 | 246 |
| Isomeric mixture feed rate (cc/hr) | 57 | 41 | 90 | 148 | 33 | 33 |
| Baffinate discharge rate (cc/hr) | 173 | 147 | 76 | 272 | 171 | 196 |
| Liquid flow rate (cc/hr) | | | | | | |
| L(I) in desorbing zone | 998 | 883 | 982 | 1063 | 1145 | 982 |
| L(II) in concentrating zone | 867 | 859 | 736 | 875 | 990 | 736 |
| L(III) in adsorption zone | 924 | 900 | 826 | 1023 | 1023 | 769 |
| L(IV) in recovery zone | 751 | 753 | 750 | 751 | 852 | 573 |
| L(I)/S(I) | 1.22 | 1.08 | 1.20 | 1.30 | 1.40 | 1.20 |
| L(II)/S(II) | 1.06 | 1.05 | 0.90 | 1.07 | 1.21 | 0.90 |
| L(III)/S(III) | 1.13 | 1.10 | 1.01 | 1.25 | 1.25 | 0.94 |
| L(IV)/S(IV) | 0.92 | 0.92 | 0.92 | 0.92 | 1.10 | 0.70 |
| Purity of 2,7-DIPN (wt. %) | 99.2 | 98.1 | 53.1 | 98.0 | 35.1 | 32.1 |
| Recovery rate of 2,7-DIPN (wt. %) | 95.7 | 65.1 | 95.3 | 42.1 | 64.2 | 98.0 |

In Experiment No. 2, in which L(I)/S(I) is excessively small, the 2,7-DIPN is carried by the absorbent and is recirculated into the raffinate, so that the recovery rate thereof is decreased. In Experiment No. 3, in which L(II)/S(II) is excessively small, isomers other than the 2,7-DIPN contaminate the extract so that the purity of the 2,7-DIPN is reduced. Since, in Experiment No. 4, L(III)/S(III) is excessively large, the 2,7-DIPN enters the raffinate flow to reduce the recovery rate. Too large an L(IV)/S(IV) in Experiment No. 5 causes isomers other than the 2,7-DIPN to contaminate the recovered desorbent material and, therefore, the extract. This lowers the purity of the 2,7-DIPN product. In Experiment No. 6, on the other hand, the L(IV)/S(IV) is so small that isomers other than 2,7-DIPN contaminate the extract to cause reduction of the purity of the 2,7-DIPN product.

EXAMPLE 9

The isomeric mixture having the composition shown in Table 16 is subjected to an adsorption treatment in the same manner as that in Example 6 using the absorbent No. 1 (K-Y-zeolite). The relative separation factors were as shown in Table 22.

TABLE 22

| Absorbent | Relative Separation Factor B | | | | | | |
|---|---|---|---|---|---|---|---|
| | (2,7/ 1,3) | (2,7/ 1,7) | (2,7/ 1,5) | (2,7/ 1,4) | (2,7/ 1,6) | (2,7/ 2,3) | (2,7/ 2,6) |
| No. 1 | 21.0 | 0.8 | 2.3 | 9.4 | 10.3 | 5.4 | 19.3 |

The above results show that 1,7-DIPN can be separated together with the 2,7-DIPN by adsorption. Since there exists a difference of 8° C. in boiling point between them (see Table 16), they can be separated from each other by distillation.

It was confirmed that when the isomeric mixture of Table 16 from which 2,7- and 1,7-DIPN had been removed by adsorption as above was subjected to precipitation in the same manner as that in Example 6, the 2,6-DIPN was able to be separated as crystals with a high purity.

EXAMPLE 10

The raffinate obtained in Example 8, Experiment No. 1 was distilled to remove the desorbent material, thereby to obtain a mixture having the composition shown in Table 23.

TABLE 23

| Component | Content (% by weight) |
|---|---|
| 1,5-DIPN | 1.4 |
| 1,4-DIPN | 9.1 |
| 2,7-DIPN | 1.8 |
| 1,6-DIPN | 34.4 |
| 2,3-DIPN | 10.7 |
| 2,6-DIPN | 41.0 |
| others | 1.5 |

The above mixture was then subjected to an adsorption and desorption separation treatment for the removal of 2,6-DIPN using a simulated, countercurrent moving bed system as shown in FIG. 3. Absorbent No. 2 (Na-type Y-zeolite) was packed in 16 column chambers No. 101–116 (each inside volume: 70 ml). In the first stage, the isomeric mixture was fed at a feed rate of 25 ml/hr through the line 119, a desorbent material (diethylbenzene) at a feed rate of 80 ml/hr through the line 117, while simultaneously discharging an extract through the line 118 at a rate of 70 ml/hr and a raffinate through the line 120 at a rate of 35 ml. The points of the feeding and discharging were shifted downward from one chamber to the adjacent downstream chamber with an interval of 480 seconds. The 2,6-DIPN was recovered as an extract with a purity of 99 wt % (desorbent free basis) and a yield of 90 wt %.

EXAMPLE 11

About 100 g of the isomeric mixture having the composition shown in Table 23 was mixed with about 30 g of n-heptane and the mixture was cooled at 0° C. for crystallization. About 25 g of the 2,6-DIPN was obtained as crystals with a purity of 97.9 wt %.

EXAMPLE 12

The isomeric mixture (5.3 g) having the composition shown in Table 3 was mixed with 74.3 g of methanol and 18.9 g of thiourea and the mixture was stirred at 60° C. for 30 minutes. The resulting mixture was allowed to stand and to be gradually cooled to room temperature and then kept at −5° C. for 18 hours. As a consequence, there was obtained a urea adduct. This adduct was filtered and washed with methyl ether and then decomposed with distilled water. Extraction of the decomposed mixture with benzene gave 2,6-DIPN with a purity of 95.3 wt % and a yield of 81.6%.

EXAMPLE 13

The 1,3- and 1,7-DIPN-free isomeric mixture having the composition shown in Table 24 was subjected to an adsorption and desorption separation treatment for the removal of 2,7-DIPN using a simulated, countercurrent moving bed system as shown in FIG. 3.

TABLE 24

| Component | Content (% by weight) |
|---|---|
| 1,5-DIPN | 0.3 |
| 1,4-DIPN | 0.3 |
| 2,7-DIPN | 40.6 |
| 1,6-DIPN | 8.3 |
| 2,3-DIPN | 0.5 |
| 2,6-DIPN | 48.7 |
| others | 1.3 |

Absorbent No. 1 (K-type Y-zeolite) was packed in 16 column chambers No. 101–116 (each inside volume: 70 ml). In the first stage, the isomeric mixture was fed at a feed rate of 30 ml/hr through the line 119, a desorbent material (diethylbenzene) at a feed rate of 113 ml/hr through the line 117, while discharging an extract through the line 118 at a rate of 45 ml/hr and raffinate through the line 120 at a rate of 98 ml. The points of the feeding and discharging were shifted downward from one chamber to the adjacent downstream chamber with an interval of 370 seconds. The 2,7-DIPN was recovered as an extract with a purity of 99.5 wt % (desorbent free basis) and recovery rate (yield) of 99.1 wt %. The thus obtained raffinate was distilled to remove the desorbent material and 100 g of the resulting isomeric mixture were cooled in the same manner as that in Example 6 to obtain about 70 g of 2,6-DIPN crystals with purity of 98.7 wt %.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process for the production of 2,6-diisopropylnaphthalene, comprising the steps of:
   (a) reacting a monoisopropylnaphthalene-containing feed with propylene to obtain a first mixture containing isopropylated naphthalenes;
   (b) subjecting said first mixture to transalkylation with a triisopropylnaphthalene-containing mixture to obtain a second mixture containing mono-, di- and tri-isopropylnaphthalenes;
   (c) separating said second mixture by a first distillation into a first fraction containing monoisopropylnaphthalenes, a second fraction having a higher boiling point than that of said first fraction and containing diisopropylnaphthalenes and a third fraction having a boiling point higher than that of said second fraction and containing triisopropylnaphthalenes;

(d) recycling at least part of said third fraction to step (b) as said triisopropylnaphthalene-containing mixture;

(e) separating said second fraction into a first product rich in 2,6-diisopropylnaphthalene and a second product rich in diisopropylnaphthalenes other than 2,6-diisopropylnaphthalene;

(f) subjecting said second product to transalkylation with naphthalene to obtain a third mixture containing monoisopropylnaphthalenes; and (g) recycling said third mixture to step (a), as at least a portion of said monoisopropylnaphthalene-containing feed, and/or step (c) with the proviso that when said third mixture is recycled only to step (c), at least part of said first fraction obtained in step (c) is recycled to step (a) as said monoisopropylnaphthalene-containing feed.

2. A process as claimed in claim 1, further comprising recycling said first fraction obtained in step (c) to at least one of steps (a), (b) and (f).

3. A process as claimed in claim 1, further comprising separating said first fraction into a light fraction and a heavy fraction, and recycling said light fraction to step (a) as at least a portion of said monoisopropylnaphthalene-containing feed.

4. A process as claimed in claim 1, further comprising separating said third fraction into a light fraction and a heavy fraction, said light fraction being recycled to step (b) as said triisopropylnaphthalene-containing mixture.

5. A process as claimed in claim 1, wherein step (a) is performed in the presence of a solid acid catalyst at a temperature of 150°–250° C. under a pressure so that naphthalene is present as a liquid.

6. A process as claimed in claim 1, wherein step (b) is performed in the presence of a solid acid catalyst at a temperature of 250°–300° C. under a pressure so that unreacted naphthalene is present as a vapor.

7. A process as claimed in claim 1, wherein step (f) is performed in the presence of a solid acid catalyst at a temperature of 250°–300° C. under a pressure so that the naphthalene is present substantially as a vapor.

8. A process as claimed in claim 1, wherein step (e) includes the sub-steps of:

(h) subjecting said second fraction to a second distillation treatment to separate same into a fourth fraction rich in 1,7- and 1,3-diisopropylnaphthalenes and a fifth fraction containing the remainder of the diisopropylnaphthalenes fed to said second distillation;

(j) subjecting said fifth fraction to a selective absorption and desorption treatment which comprises:

(i) contacting said fifth fraction with a solid absorbent contained in an adsorption zone, maintained at adsorption conditions and capable of selectively absorbing 2,7-diisopropylnaphthalene, thereby to effect selective adsorption of 2,7-diisopropylnaphthalene contained in said fifth fraction;

(ii) withdrawing from the adsorption zone a raffinate containing non-sorbed diisopropylnaphthalenes as said second product;

(iii) contacting said solid absorbent maintained at desorption conditions with a desorbent material to effect removal of the 2,7-diisopropylnaphthalene therefrom; and

(iv) withdrawing from said solid adsorbent an extract containing the removed 2,7-diisopropylnaphthalene;

(k) separating said raffinate into a third product stripped of 2,6-diisopropylnaphthalene; and (m) feeding said fourth fraction and said third product to step (f) as said second product.

9. A process as claimed in claim 8, wherein said solid absorbent is a potassium-substituted Y-zeolite.

10. A process as claimed in claim 8, wherein said desorbent material is an alkylbenzene of the formula:

$(R')_n$—Ph—R wherein Ph represents a benzene nucleus, R and R' represent independently from each other a methyl, an ethyl, an n-propyl or an isopropyl, and n is an integer of 0 or 1.

11. A process as claimed in claim 8, wherein step (j) includes the steps of:

providing a simulated countercurrent moving bed system which includes a fixed bed of the solid absorbent containing at least four serially interconnected zones having fluid flow connecting means between adjacent zones and between the outlet of the last zone and the inlet of the first zone in the series, to thereby provide cyclic fluid flow in said system;

introducing said fifth fraction into one sorbing zone of said fixed bed to selectively sorb the 2,7-diisopropylnaphthalene contained in said fifth fraction;

introducing a desorbent material to another, desorbing zone of said fixed bed to remove the sorbed 2,7-diisopropylnaphthalene, said desorbing zone being positioned upstream of said sorbing zone such that an intermediate, concentrating zone is defined between said sorbing and desorbing zones and downstream of said desorbing zone and that a recovering zone is defined downstream of said sorbing zone;

withdrawing the raffinate containing non-sorbed diisopropylnaphthalenes from the fluid flow connecting means extending between said sorbing and recovering zones;

withdrawing the extract containing the removed 2,7-diisopropylnaphthalene from the fluid flow connecting means extending between said desorbing and concentrating zones; and periodically advancing downstream the point of introducing said fifth fraction, while simultaneously and equally advancing the points of introducing the desorbent material and of withdrawing the raffinate and the extract, said desorbing, concentrating, sorbing and recovering zones being operated under conditions satisfying the following formulas:

desorbing zone: $L(I)/S(I) > 0.2 + L(IV)/S(I)$
concentrating zone: $L(II)/S(II) > 0.1 + L(IV)/S(II)$
sorbing zone: $L(III)/S(III) < 0.3 + L(IV)/S(III)$
recovering zone: $0.8 \ L(IV)/S(IV) < 1.0$ wherein $L(I)$ through $L(IV)$ represent the flow rates, in terms of cc/hour, of liquids flowing through said desorbing zone, concentrating zone, sorbing zone and recovering zone, respectively, and $S(I)$ through $S(IV)$ represent the simulate moving rates, in terms of cc/hour, of the absorbent through said desorbing zone, concentrating zone, sorbing zone and recovering zone, respectively.

12. A process as claimed in claim 1, wherein step (e) includes the substeps of:

(h) subjecting said second fraction to a first, selective absorption and desorption treatment which comprises:
  (i) contacting said second fraction with a mass of a first solid absorbent contained in a first adsorption zone and capable of selectively absorbing 1,7 and 2,7-diisopropylnaphthalenes to effect selective adsorption of 1,7 and 2,7-diisopropylnaphthalene contained in said second fraction;
  (ii) withdrawing from the first adsorption zone a first raffinate;
  (iii) contacting said first solid absorbent with a first desorbent material to effect removal of the 1,7 and 2,7-diisopropylnaphthalenes therefrom; and
  (iv) withdrawing from said first solid absorbent an extract containing the desorbent material and the removed 1,7- and 2,7-diisopropylnaphthalenes as a third product;
(j) subjecting said first raffinate to a second, selective absorption and desorption treatment which comprises:
  (v) contacting said first raffinate with a mass of a second solid absorbent contained in a second adsorption zone and capable of selectively absorbing 2,6-diisopropylnaphthalene to effect selective adsorption of 2,6-diisopropylnaphthalene contained in said first raffinate;
  (vi) withdrawing from the second adsorption zone a second raffinate;
  (vii) contacting said second solid absorbent with a second desorbent material to effect removal of the 2,6-diisopropylnaphthalene therefrom; and
  (viii) withdrawing from said second solid absorbent an extract containing the removed 2,6-diisopropylnaphthalene as the first product; and
(k) feeding said third product and said second raffinate to step (f) as said second product.

13. A process as claimed in claim 12, wherein said first and second solid absorbents are each a potassium-substituted Y-zeolite.

14. A process as claimed in claim 12, wherein said first and second desorbent materials are each an alkylbenzene of the formula:

$(R')_n$—Ph—R wherein Ph represents a benzene nucleus, R and R' represent independently from each other a methyl, an ethyl, an n-propyl or an isopropyl, and n is an integer of 0 or 1.

15. A process as claimed in claim 12, wherein step (h) includes the steps of:
providing a simulated countercurrent moving bed system which includes a fixed bed of said first solid absorbent containing least four serially interconnected zones having fluid flow connecting means between adjacent zones and between the outlet of the last zone and the inlet of the first zone in the series, to thereby provide cyclic fluid flow in said system;
introducing said second fraction into one sorbing zone of said fixed bed to selectively sorb the 1,7- and 2,7-diisopropylnaphthalenes contained in said second fraction;
introducing the first desorbent material to another, desorbing zone of said fixed bed to remove the sorbed 1,7 and 2,7-diisopropylnaphthalenes, said desorbing zone being positioned upstream of said sorbing zone such that an intermediate, concentrating zone is defined between said sorbing and desorbing zones and downstream of said desorbing zone and that a recovering zone is defined downstream of said sorbing zone;
withdrawing the first raffinate containing non-sorbed diisopropylnaphthalenes from the fluid flow connecting means extending between said sorbing and recovering zones;
withdrawing an extract containing the removed 1,7- and 2,7-diisopropylnaphthalenes from the fluid flow connecting means extending between said desorbing and concentrating zones as said third product; and
periodically advancing downstream the point of introducing said second fraction, while simultaneously and equally advancing the points of introducing the desorbent material and of withdrawing the raffinate and the extract,
said desorbing, concentrating, sorbing and recovering zones being operated under conditions satisfying the following formulas:
desorbing zone: $L(I)/S(I) > 0.2 + L(IV)/S(I)$
concentrating zone: $L(II)/S(II) > 0.1 + L(IV)/S(II)$
sorbing zone: $L(III)/S(III) < 0.3 + L(IV)/S(III)$
recovering zone: $0.8 < L(IV)/S(IV) < 1.0$
wherein $L(I)$ through $L(IV)$ represent the flow rates, in terms of cc/hour, of liquids flowing through said desorbing zone, concentrating zone, sorbing zone and recovering zone, respectively, and $S(I)$ through $S(IV)$ represent the simulate moving rates, in terms of cc/hour, of the absorbent through said desorbing zone, concentrating zone, sorbing zone and recovering zone, respectively.

16. A process as claimed in claim 12, wherein step (j) includes the steps of:
providing a simulated countercurrent moving bed system which includes a fixed bed of said second solid absorbent containing at least four serially interconnected zones having fluid flow connecting means between adjacent zones and between the outlet of the last zone and the inlet of the first zone in the series, to thereby provide cyclic fluid flow in said system;
introducing said first raffinate into one sorbing zone of said fixed bed to selectively sorb the 2,6-diisopropylnaphthalene contained in said first raffinate;
introducing the second desorbent material to another, desorbing zone of said fixed bed to remove the sorbed 1,7 and 2,7-diisopropylnaphthalenes, said desorbing zone being positioned upstream of said sorbing zone such that an intermediate, concentrating zone is defined between said sorbing and desorbing zones and downstream of said desorbing zone and that a recovering zone is defined downstream of said sorbing zone;
withdrawing the second raffinate containing non-sorbed diisopropylnaphthalenes from the fluid flow connecting means extending between said sorbing and recovering zones;
withdrawing an extract containing the removed 2,6-diisopropylnaphthalenes from the fluid flow connecting means extending between said desorbing and concentrating zones as said first product; and
periodically advancing downstream the point of introducing said second fraction, while simultaneously and equally advancing the points of introducing the desorbent material and of withdrawing the raffinate and the extract, said desorbing, concentrating, sorbing and recovering zones being operated under conditions satisfying the following formulas:

desorbing zone: $L(I)/S(I) > 0.2 + L(IV)/S(I)$
concentrating zone: $L(II)/S(II) 22\ 0.1 + L(IV)/S(II)$
sorbing zone: $L(III)/S(III) < 0.3 + L(IV)/S(III)$
recovering zone: $0.8 < L(IV)/S(IV) < 1.0$ wherein $L(I)$ through $L(IV)$ represent the flow rates, in terms of cc/hour, of liquids flowing through said desorbing zone, concentrating zone, sorbing zone and recovering zone, respectively, and $S(I)$ through $S(IV)$ represent the simulate moving rates, in terms of cc/hour, of the absorbent through said desorbing zone, concentrating zone, sorbing zone and recovering zone, respectively.

17. A process for the production of diisopropylnaphthalenes, comprising the steps of:
    (a) reacting naphthalene with propylene to obtain a first mixture containing isopropylated naphthalenes, step (a) being carried out under conditions so that the molar ratio of the isopropyl group of the isopropylated naphthalenes to the the isopropylated naphthalenes and unreacted naphthalene contained in said first mixture is in the range of 1.3 : 1 to 1.8 : 1;
    (b) subjecting said first mixture to transalkylation with a triisopropylnaphthalene-containing mixture to obtain a second mixture containing mono-, di- and tri-isopropylnaphthalenes;
    (c) separating said second mixture by distillation into a first fraction containing monoisopropylnaphthalenes, a second fraction having a higher boiling point than that of said first fraction and containing diisopropyl-naphthalenes and a third fraction having a boiling point higher than that of said second fraction and containing triisopropylnaphthalenes;
    (d) recycling at least part of said third fraction to step (b) as said triisopropylnaphthalene-containing mixture; and
    (e) recycling at least part of said first fraction to step (a) and/or step (b).

18. A process as claimed in claim 17, further comprising separating 2,6-diisopropylnaphthalene from said second fraction.

19. A process as claimed in claim 18, further comprising recycling said second fraction from which 2,6-diisopropylnaphthalene has been removed into step (b).

20. A process as claimed in claim 17, wherein step (a) is performed in the presence of a solid acid catalyst at a temperature of 150°–250° C. under a pressure so that the naphthalene is present as a liquid.

21. A process as claimed in claim 17, wherein step (b) is performed in the presence of a solid acid catalyst at a temperature of 250°–300° C. under a pressure so that unreacted naphthalene is present as a vapor.

22. A process as claimed in claim 17, wherein step (b) is carried out so that the molar ratio of the isopropylene of the isopropylated naphthalenes contained in said third mixture to the isopropylated naphthalenes and unreacted naphthalene contained in said third mixture is in the range of 1.6 : 1 to 2.0 : 1.

23. A process as claimed in claim 17, further comprising (f) separating said second fraction into a first product containing 2,7-diisopropylnaphthalene and a second product containing diisopropylnaphthalenes other than 2,7-diisopropylnaphthalene, and (g) separating said second product into a third product containing 2,6-diisopropylnaphthalene and a fourth product containing diisopropylnaphthalenes other than 2,6-diisopropylnaphthalene.

24. A process as claimed in claim 23, wherein step (f) includes (h) subjecting said second fraction to a distillation treatment to remove 1,7-and 1,3-diisopropylnaphthalenes therefrom and to obtain a fifth product containing the remainder of the diisopropylnaphthalenes fed to step (f), and then (j) subjecting said fifth product to a selective absorption and desorption treatment which comprises:
    (i) contacting said fifth product with a solid absorbent contained in an adsorption zone, maintained at adsorption conditions and capable of selectively absorbing 2,7-diisopropylnaphthalene, thereby to effect selective adsorption of 2,7-diisopropylnaphthalene contained in said fifth product;
    (ii) withdrawing from the adsorption zone a raffinate containing non-sorbed diisopropylnaphthalenes;
    (iii) contacting said solid absorbent maintained at desorption conditions with a desorbent material to effect removal of the 2,7-diisopropylnaphthalene therefrom; and
    (iv) withdrawing from said solid absorbent an extract containing the removed 2,7-diisopropylnaphthalene as said first product.

25. A process as claimed in claim 24, wherein said solid absorbent is a potassium-substituted Y-zeolite.

26. A process as claimed in claim 24, wherein said desorbent material is a alkylbenzene of the formula:

$(R')_n$—Ph—R wherein Ph represents a benzene nucleus, R and R' represent independently from each other a methyl, an ethyl, an n-propyl or an isopropyl, and n is an integer of 0 or 1.

27. A process as claimed in claim 23, wherein step (j) includes the steps of:

providing a simulated countercurrent moving bed system which includes a fixed bed of the solid absorbent containing at least four serially interconnected zones having fluid flow connecting means between adjacent zones and between the outlet of the last zone and the inlet of the first zone in the series, to thereby provide cyclic fluid flow in said system;

introducing said second fraction into one sorbing zone of said fixed bed to selectively sorb the 2,7-diisopropylnaphthalene contained in said second fraction;

introducing a desorbent material to another, desorbing zone of said fixed bed to remove the sorbed 2,7diisopropylnaphthalene, said desorbing zone being positioned upstream of said sorbing zone such that an intermediate, concentrating zone is defined between said sorbing and desorbing zones and downstream of said desorbing zone and that a recovering zone is defined downstream of said sorbing zone;

withdrawing the raffinate containing non-sorbed diisopropylnaphthalenes from the fluid flow connecting means extending between said sorbing and recovering zones;

withdrawing the extract containing the removed 2,7-diisopropylnaphthalene from the fluid flow connecting means extending between said desorbing and concentrating zones as said first product; and periodically advancing downstream the point of introducing said second fraction, while simultaneously and equally advancing the points of introducing the desorbent material and of withdrawing the raffinate and the extract, said desorbing, concentrating, sorbing and recovering zones being operated under conditions satisfying the following formulas:

desorbing zone: $L(I)/S(I) > 0.2 + L(IV)/S(I)$
concentrating zone: $L(II)/S(II) > 0.1 + L(IV)/S(II)$
sorbing zone: $L(III)/S(III) < 0.3 + L(IV)/S(III)$
recovering zone: $0.8\ L(IV)/S(IV) < 1.0$ wherein L(I) through L(IV) represent the flow rates, in terms of cc/hour, of liquids flowing through said desorbing zone, concentrating zone, sorbing zone and recovering zone, respectively, and S(I) through S(IV) represent the simulate moving rates, in terms of cc/hour, of the absorbent through said desorbing zone, concentrating zone, sorbing zone and recovering zone, respectively.

28. A process as claimed in claim 23, wherein step (f) includes subjecting said second fraction to a selective absorption and desorption treatment which comprises:
(i) contacting said second fraction with a mass of a solid absorbent contained in an adsorption zone and capable of selectively absorbing 1,7 and 2,7-diisopropylnaphthalenes to effect selective adsorption of 1,7 and 2,7-diisopropylzone;
(ii) withdrawing from the adsorption zone a raffinate;
(iii) contacting said solid absorbent with a desorbent material to effect removal of the 1,7 and 2,7-diisopropylnaphthalenes therefrom; and
(iv) withdrawing from said solid absorbent an extract containing the desorbent material and the removed 1,7 and 2,7-diisopropylnaphthalenes, said raffinate being fed to step (j).

29. A process as claimed in claim 28, wherein said solid absorbent is a potassium-substituted Y-zeolite.

30. A process as claimed in claim 28, wherein said desorbent material is an alkylbenzene of the formula:

$(R')_n$—Ph—R wherein Ph represents a benzene nucleus, R and R' represent independently from each other a methyl, an ethyl, an n-propyl or an isopropyl, and n is an integer of 0 or 1.

31. A process as claimed in claim 28, wherein said selective adsorption and desorption treatment includes the steps of:

providing a simulated countercurrent moving bed system which includes a fixed bed of the solid absorbent containing at least four serially interconnected zones having fluid flow connecting means between adjacent zones and between the outlet of the last zone and the inlet of the first zone in the series, to thereby provide cyclic fluid flow in said system;

introducing said second fraction into one sorbing zone of said fixed bed to selectively sorb the 2,7-diisopropylnaphthalene contained in said second fraction;

introducing the desorbent material to another, desorbing zone of said fixed bed to remove the sorbed 2,7-diisopropyl-naphthalene, said desorbing zone being positioned upstream of said sorbing zone such that an intermediate, concentrating zone is defined between said sorbing and desorbing zones and downstream of said desorbing zone and that a recovering zone is defined downstream of said sorbing zone;

withdrawing the raffinate containing non-sorbed diisopropylnaphthalenes from the fluid flow connecting means extending between said sorbing and recovering zones;

withdrawing the extract containing the removed 2,7-diisopropylnaphthalene from the fluid flow connecting means extending between said desorbing and concentrating zones as said first product; and periodically advancing downstream the point of introducing said second fraction, while simultaneously and equally advancing the points of introducing the desorbent material and of withdrawing the raffinate and the extract, said desorbing, concentrating, sorbing and recovering zones being operated under conditions satisfying the following formulas:

desorbing zone: $L(I)/S(I) > 0.2 + L(IV)/S(I)$
concentrating zone: $L(II)/S(II) > 0.1 + L(IV)/S(II)$
sorbing zone: $L(III)/S(III) < 0.3 + L(IV)/S(III)$
recovering zone: $0.8\ L(IV)/S(IV) < 1.0$ wherein L(I) through L(IV) represent the flow rates, in terms of cc/hour, of liquids flowing through said desorbing zone, concentrating zone, sorbing zone and recovering zone, respectively, and S(I) through S(IV) represent the simulate moving rates, in terms of cc/hour, of the absorbent through said desorbing zone, concentrating zone, sorbing zone and recovering zone, respectively.

* * * * *